(12) United States Patent
Hsu et al.

(10) Patent No.: US 6,579,322 B1
(45) Date of Patent: Jun. 17, 2003

(54) BIOMEDICAL MATERIAL FOR IMPROVING THE ADHESION AND PROLIFERATION OF CELLS AND A MODIFIED ARTIFICIAL VESSEL

(75) Inventors: Shan-Hui Hsu, Taichung (TW); David Chanhen Chen, Taichung (TW)

(73) Assignee: National Science Council, Taipei (TW)

( * ) Notice: Subject to any disclaimer, the term of this patent is extended or adjusted under 35 U.S.C. 154(b) by 0 days.

(21) Appl. No.: 09/420,818

(22) Filed: Oct. 19, 1999

(30) Foreign Application Priority Data

Jun. 25, 1999 (TW) ........................... 88110721 A

(51) Int. Cl.[7] ................................. A61F 2/36
(52) U.S. Cl. ............... 623/23.76; 623/1.48; 427/2.24; 427/2.25
(58) Field of Search .................. 435/69.1, 252.3; 623/1.48, 23.76; 427/2.24, 2.25; 606/76

(56) References Cited

U.S. PATENT DOCUMENTS 5,514,581 A    5/1996  Ferrari et al. ............ 435/252.3
6,407,208 B1 *  6/2002  Chen et al. ................ 530/350

OTHER PUBLICATIONS

Lin, H. et al. "Synthesis, surface, and cell–adhesion properties of polyurethanes containing covalently grafted RGD–peptides"; Mar. 1994; Journal of Biomedical Materials Research; vol. 28, No. 3, pp. 329–342.*

Lin, H. et al. "Surface properties of RGD–peptide grafted polyurethane block copolymers: Variable take–off angle and cold–stage ESCA studies"; 1993; Journal of Biomaterials Science Polymer Edition; vol. 4, No. 3, pp. 183–198.*

"Adhesion of Mammalian Cells to a Recombinant Attachment Factor, CBD/RGD, Analyzed by Image Analysis" by A. Wierzba, U. Reichl, R. Turner, R. Warren, and D. Kilburn; Biotechnology and Bioengineering, vol. 46, pp. 185–193 (1995); John Wiley & Sons, Inc.*

"Production and Properties of a Bifunctional Fusion Protein that Mediates Attachment of Vero Cells to Cellulosic Matrices"; A. Wierzba, U. Reichl,R. Turner,R. Warren,D. Kilburn; Biotechnology and Bioengineering, vol. 46,pp. 185–193(1995);John Wiley & Sons, Inc.*

Glass, J. et al. "Cell Attachment and Motility on Materials Modified by Surface–active RGD–containing Peptides". Annals of the New York Academy of Sciences; 1994 745: pp. 177–186.*

* cited by examiner

Primary Examiner—David J. Isabella
Assistant Examiner—Urmi Chattopadhyay
(74) Attorney, Agent, or Firm—Fish & Richardson P.C.

(57) ABSTRACT

A novel biomedical material, which is characterized by coating a genetically engineered CBD-RGD peptide layer on the surface of a biomedical material consisting of PU to improve the attachment of tissue cells, such as fibroblasts, epithelial cells and endothelial cells. A modified artificial vessel is also disclosed, wherein the adherence of endothelial cells is enhanced by coating a genetically engineered CBD-RGD containing peptide layer on the inner surface of the artificial vessels pre-modified by cross-linked gelatin, and the adhering capacity and activation of platelets is reduced.

6 Claims, 3 Drawing Sheets

BIOMEDICAL MATERIAL FOR IMPROVING THE ADHESION AND PROLIFERATION OF CELLS AND A MODIFIED ARTIFICIAL VESSEL

FIELD OF THE INVENTION

This invention relates to a biomedical material and an artificial vessel, and in particular relates to a biomedical material for improving the adhesion and proliferation of cells and a modified artificial vessel.

BACKGROUND OF THE INVENTION

Since PU (polyurethane) material has good mechanical property and bio-compatibility, it is widely used as a tissue substituent. However, it's hard for cells to adhere onto the PU surface, let alone proliferate thereon. Therefore, the application of PU in tissue reconstruction, such as tissue repair, is limited.

For example, during the development of artificial skin or vessels composed of PU, the tissue cells (e.g. epithelial cells or endothelial cells) are usually first seeded on the surfaces of the PU material. In order to improve the adherence of cells on the PU material, the surfaces of the PU material have to be modified. One of the modification methods for the surfaces of the PU material is reactive graft, but the reaction conditions and the reproductivities are hard to control. Another method is to modify the surfaces of the PU material by plasma. However, the required plasma instruments are expensive, and each PU material has different structure and molecular weight, thus the period for plasma modification depends on various PU materials and tissue cells desired to attach and proliferate thereon.

It is easy and convenient to improve the attachment between the tissue cells and the biomedical materials consisting of PU by using adhering molecules consisting of protein or peptide. This method is based on the intracellular substance, which can regulate the adhesion, migration and growth of cells through the interaction with intergrins locating on the outer cell membranes. The adhering molecules of cells described above consist of proteins or peptides, which interact with intergrins locating on the outer membrane of cells. Therefore, these adhering molecules consisting of proteins or peptides can be used to enhance the attachment of cells. The amino acid sequences of these adhesion molecules all contain Arg-Gly-Asp (RGD), thus these adhering molecules are abbreviated as RGD-containing peptides or proteins.

Fibronectin is one of the natural RGD-containing peptides. Commercial fibronectin is very expensive because most of the commercial fibronectins are purified from plasma. Alternatively, RGD-containing peptides can be obtained by chemical synthesis or genetic engineering. However, chemical synthesis can only produce water-soluble RGD-containing peptides with low molecular weight (e.g. the peptide consisting of only six amino acids), which will associate with the intergrins and thus inhibit the attachment of cells. Therefore, it is necessary to develop a chemically immobilized peptide or high M. W. RGD-containing peptide.

Moreover, by using genetic engineering techniques, the high M. W. RGD-containing peptides or proteins can be mass-produced by microorganisms. A method for producing a chimeric protein, CBD-RGD, which contains a cellulose-binding domain (CBD), was disclosed by one inventor (David Chen) of this present invention [TW Patent Application No. 86114750 and U.S. patent application Ser. No. 09/166,966], wherein the gene encoding this CBD-containing chimeric protein was cloned into a vector to construct an expression vector. Then, this constructed expression vector was transferred into microorganisms, preferably E. coli., to mass-express the chimeric CBD-RGD containing protein encoded by this expression vector. Thus, a large amount of cheap CBD-RGD containing protein was recovered from the culture medium.

In accordance, in order to enhance the adhering ability and growing rate of tissue repairing cells on PU materials, this present invention discloses a novel tissue repairing biomaterial modified by the CBD-RGD containing peptide or protein produced according to the method disclosed in TW Patent Application No. 8611475 and U.S. patent application Ser. No. 09/166,966.

Moreover, the CBD-RGD containing peptide or protein can cooperate with cross-linked gelatin to modify the inner surface of the artificial vessel, and improve the adhesion and proliferation of endothelial cells on the inner surface of the artificial vessel. Also, the adhesion ability and the average degree of activation of platelets on the inner surface of the modified artificial vessel can be reduced.

SUMMARY OF THE INVENTION

This invention discloses a novel biomedical material, characterized by coating a genetically engineered CBD-RGD containing peptide layer on the surface of the biomedical material consisting of PU to improve the adherence of tissue cells on the biomedical material. Moreover, this invention discloses a modified artificial vessel, wherein the adherence of endothelial cells can be enhanced by coating a CBD-RGD containing peptide layer on the inner surface of the artificial vessels pre-modified by cross-linked gelatin. In addition, the adherence and activation of platelets on the modified vessel according to this invention can be reduced.

Other feature and advantages of the invention will be apparent from the following detailed description, and from the claims.

DETAILED DESCRIPTION OF THE INVENTION

Figure 1A:
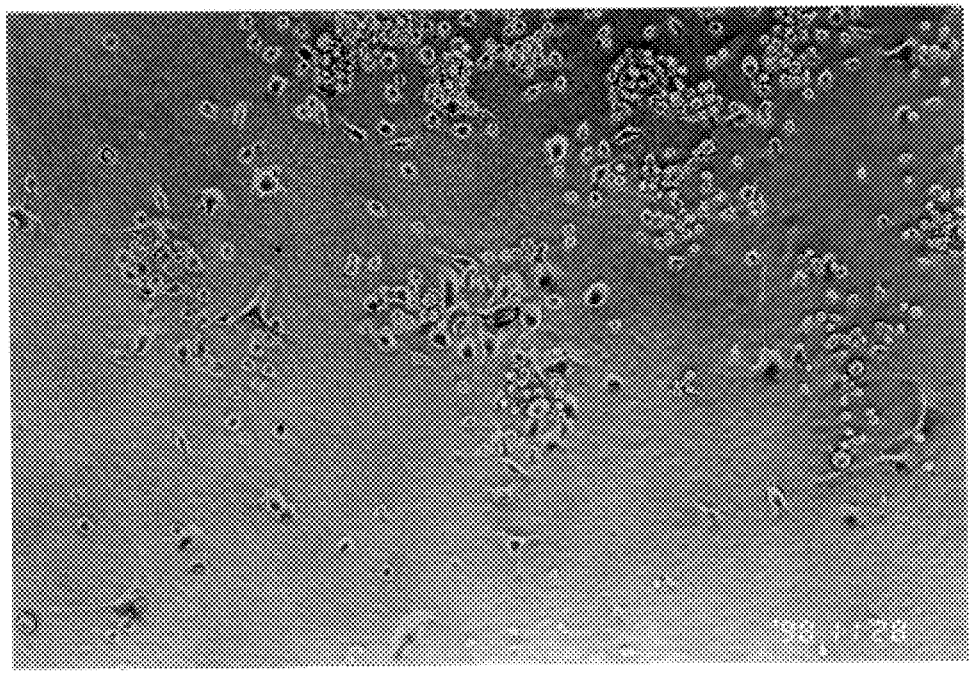
FIGS. 1A and 1B respectively show the adhesion morphology of fibroblasts on an unmodified PU slide and a modified PU slide according to Embodiment 1 of this invention.

One feature of this invention discloses a biomedical material for improving the adhesion and proliferation of tissue cells. The biomedical material comprises a biomedical substrate for cells to attach thereon, and a surface modifier consisting of CBD-RGD containing peptide coated on the surface of the biomedical substrate. The biomedical substrate consists of PU, and the obtained biomedical material is a tissue culture plate. Moreover, the molecular weight of the CBD-RGD containing peptide is 13 kDa. The tissue cells can be selected from one of the group consisting of fibroblasts, epithelial cells and endothelial cells.

Another feature of this invention discloses a method for making the biomedical material for improving the adhesion and proliferation of tissue cells. The method begins with providing a biomedical substrate for cells to attach thereon, then a CBD-RGD containing peptide layer is coated on the biomedical substrate. The biomedical material is a tissue culture plate, and the molecular weight of the CBD-RGD containing peptide is 13 kDa. The tissue cells can be selected from one of the group consisting of fibroblasts, epithelial cells and endothelial cells.

Another feature of this invention discloses a modified artificial vessel. The modified artificial vessel comprises an artificial vessel consisting of a biomedical acceptable polymer, an inner and outer cross-linked gelatin layers respectively coated on the inner and outer surfaces of the artificial vessel, and a CBD-RGD containing peptide layer coated on the inner cross-linked gelatin layer. As described above, the biomedical acceptable polymer consists of PU. The cross-linked gelatin layer is composed of the cross-linked product of gelatin and epoxide, wherein the molecular weight of the gelatin is 80 kDa, and the epoxide consists of DENACOL ($C_8H_{14}O_4$). The molecular weight of the CBD-RGD is 13 kDa.

Another feature of this invention discloses a method for making the modified artificial vessel, the steps comprising: (a) providing a artificial vessel consisting of a biomedical acceptable material; (b) dipping the artificial vessel in a warm gelatin solution for a period of time; (c) removing the artificial vessel, and cooling to allow an inner gelatin layer and an outer gelatin layer respectively coat on the inner and outer surfaces of the artificial vessel; (d) dipping the artificial vessel obtained the step (c) into an epoxide solution, where light is filtered, to form an inner cross-linked gelatin layer and an outer cross-linked gelatin layer through the cross-linked reaction between the epoxide and both of the gelatin layers; (e) introducing the CBD-RGD containing peptide solution into the artificial vessel, and setting in a suitable temperature to form a CBD-RGD containing peptide layer on the inner gelatin layer; and (f) removing the CBD-RGD containing peptide solution within the artificial vessel, and obtaining a artificial vessel modified by the inner and outer cross-linked gelatin layers and the CBD-RGD on the inner cross-linked gelatin.

As described above, the biomedical acceptable polymer consists of PU. The inner and outer cross-linked gelatin layers are composed of the cross-linked product of gelatin and epoxide, wherein the molecular weight of the gelatin is 80 kDa, and the epoxide consists of DENACOL ($C_8H_{14}O_4$). The molecular weight of the CBD-RGD containing peptide is approximately 13 kDa.

EMBODIMENT OF THE INVENTION

Example 1

Biomedical Material Consisting of CBD-RGD Modified PU

Material

The PU materials, including PELLETHANE 2363-80A, PELLETHANE 2103-80A or CARDIOMAT can be commercially obtained from Upjohn (Torrance, Calif.). Alternatively, the PU material can be obtained by polymerizing the diphenyl methane di-isocyanate with polyether glycols.

CBD-RGD protein was prepared according to the previous patent application (TW Patent Application No. 86114750 and U.S. patent application Ser. No. 09/166,966). The CBD-RGD stock solution (0.19 mg/ml, 98%) [200 mM Tris-HCl (pH=7.4), 100 mM NaCl, 20 mM $CaCl_2$] remains active after storage in a freezer (−18° C.) for half a year. This CBD-RGD stock solution was warmed to room temperature when used.

Modification of the Surface of the PU Material

This invention is characterized by modifying the surface of the PU material by coating a CBD-RGD containing peptide layer to improve the adhesion ability of cells. The coating was completed by dropping 20 μl of a sterile CBD-RGD containing peptide solution in the center of a PU slide, and allowing the CBD-RGD containing peptide solution to cover the whole surface of the slide. Then, this slide was placed in a laminar flow-system for 30 minutes to obtain a CBD-RGD modified PU slide. The CBD-RGD containing peptide is directly and non-covalently coated onto the surface of the PU slide.

Adherence Test

In order to test the difference of the adherence and growth of cells on PU materials with or without modification, fibroblasts (ATCC NCTC clone 929), epithelial cells (ATCC MDBK) and endothelial cells (ATCC ECV304) were chosen in this test.

First, the CBD-RGD modified PU slides were placed in each well of a 24-well microplate. Then, 1 ml of suspension containing $5 \times 10^4$ cells (either fibroblasts, epithelial cells or endothelial cells) was introduced into each well, and incubated in a 5% $CO_2$/95% air incubator at 37° C. The culture medium used for cultivating the fibroblasts and epithelial cells was DMEM supplied with 10% FCS; the culture medium used for cultivating the endothelial cells was Medium-199 supplied with 10% FCS. During incubation, the stretch of cells was observed by a phase-contrast microscope. After various incubating intervals (3, 12, 48 hours), the culture medium was subduced, then the slide was washed slightly. The cells adhered on the slide were trypsinized by a trypsin-EDTA solution (TE-solution). Then, the TE solution was neutralized by the culture medium. Afterwards, the cells were re-suspended in a fresh medium and counted by a cell counter. The data obtained from the cell counter was analyzed by Student's t-test.

Result

The numbers of fibroblasts adherenced on the unmodified slide (X) or on the modified slide (Y) through various incubation intervals (3, 12, 48 hours) are recorded in Table 1.

TABLE 1

|  | Incubation interval | | |
| --- | --- | --- | --- |
|  | 3 hours | 12 hours | 48 hours |
| Number of fibroblasts adhered on unmodified PU slide (X) (×$10^4$) | 0.5 ± 0.1 | 3.7 ± 0.3 | 4.6 ± 0.1 |
| Number of fibroblasts adhered on PU slide modified with CBD-RGD containing peptide (Y) (×$10^4$) | 2.6 ± 0.1* | 4.6 ± 0.2* | 8.3 ± 0.4* |
| Improving fold (Y/X) | 5.2 ± 0.7* | 1.3 ± 0.2* | 1.8 ± 0.2* |

*p < 0.001

As shown in Table 1, after 3 hours incubation, the number of fibroblasts adhered on PU slide modified with CBD-RGD containing peptide was 5 fold of the number of fibroblasts adhered on unmodified PU slide. Both the numbers of fibroblasts adhered on unmodified PU slide or modified PU slide increased with incubation intervals. In addition, after 48 hours incubation, the growth of the fibroblasts adhered on PU slide modified with CBD-RGD containing peptide was 80% higher than that of the fibroblasts adhered on unmodified PU. Since the growth of fibroblasts was 80% enhanced after 48 hours incubation, the improvement of the fold of long-term incubation was less significant than that of short-term incubation. Observing by phase-contrast microscope, the fibroblasts were adhered more tightly and spread more widely on PU slides modified with CBD-RGD containing peptide than on unmodified PU slides.

Comparing the fibroblasts, epithelial cells and endothelial cells incubated on unmodified PU slide with the cells incubated on PU slide modified with CBD-RGD containing peptide for 3 hours and 48 hours, the enhanced fold of adherence and growth of these cells are listed in Table 2. The enhanced fold was the ratio of the cells adhered on PU slide modified with CBD-RGD containing peptide verse the s adhered on unmodified PU slide.

TABLE 2

|  | Fibroblasts | Epithelial cells | Endothelial cells |
| --- | --- | --- | --- |
| Enhanced fold of adherence after 3 hours incubation | 5.2 ± 0.7* | 1.4 ± 0.1* | 4.1 ± 0.5* |
| Enhanced fold of growth after 48 hours incubation | 1.8 ± 0.2* | 1.3 ± 0.1* | 1.3 ± 0.1* |

*$p < 0.001$

As shown in Table 2, the adherence of endothelial cells and fibroblasts on PU slide modified with CBD-RGD containing peptide was significantly enhanced after short-term (3 hours) incubation. The epithelial cells used in this experiment quickly adhered on either unmodified PU slide or PU slide modified with CBD-RGD, thus the enhanced fold of adherence was not significant. Similarly, the growth of either fibroblasts, epithelial cells or endothelial cells was 30% to 80% enhanced after 48 hours incubation; thus the improvement of the fold of adherence after long-term (48 hours) incubation was less significant than that of short-term (3 hours) incubation.

Figure 1B:
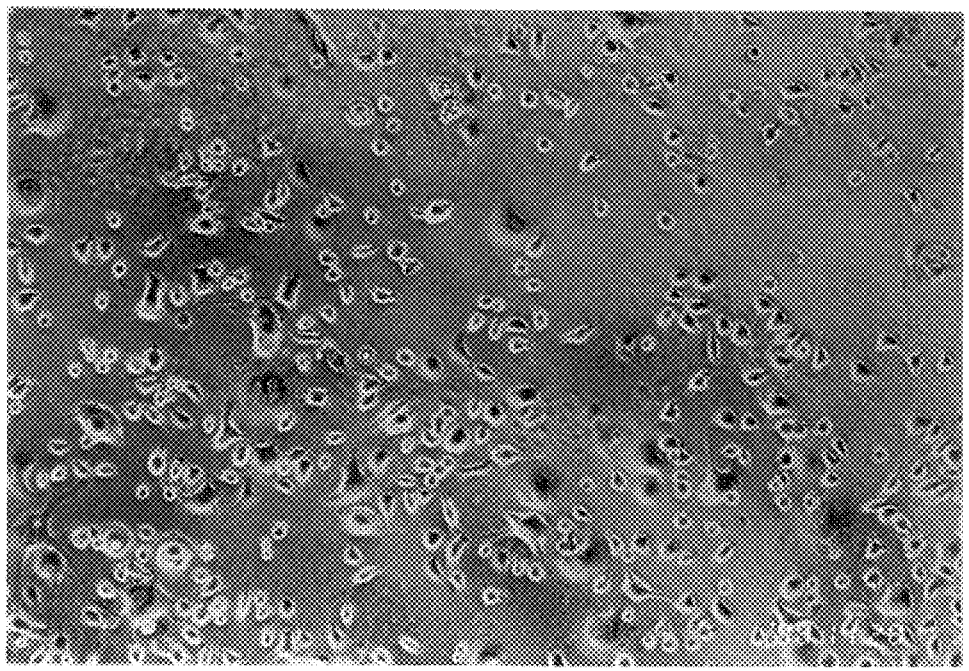
Figure 2A:
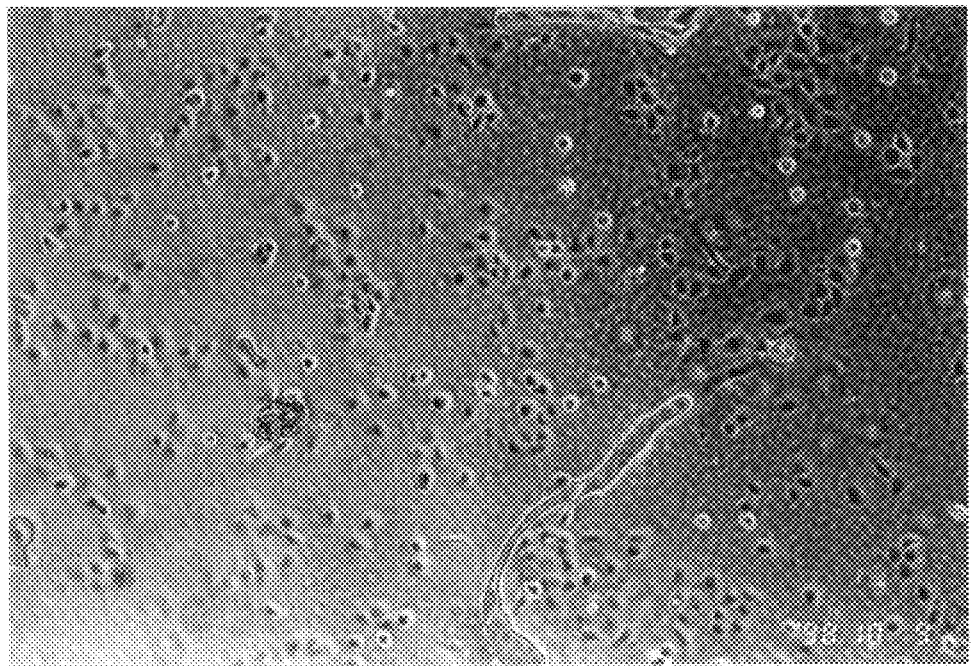
FIGS. 2A and 2B respectively show the adhesion morphology of epithelial cells on an unmodified PU slide and a modified PU slide according to Embodiment 1 of this invention.
Figure 2B:
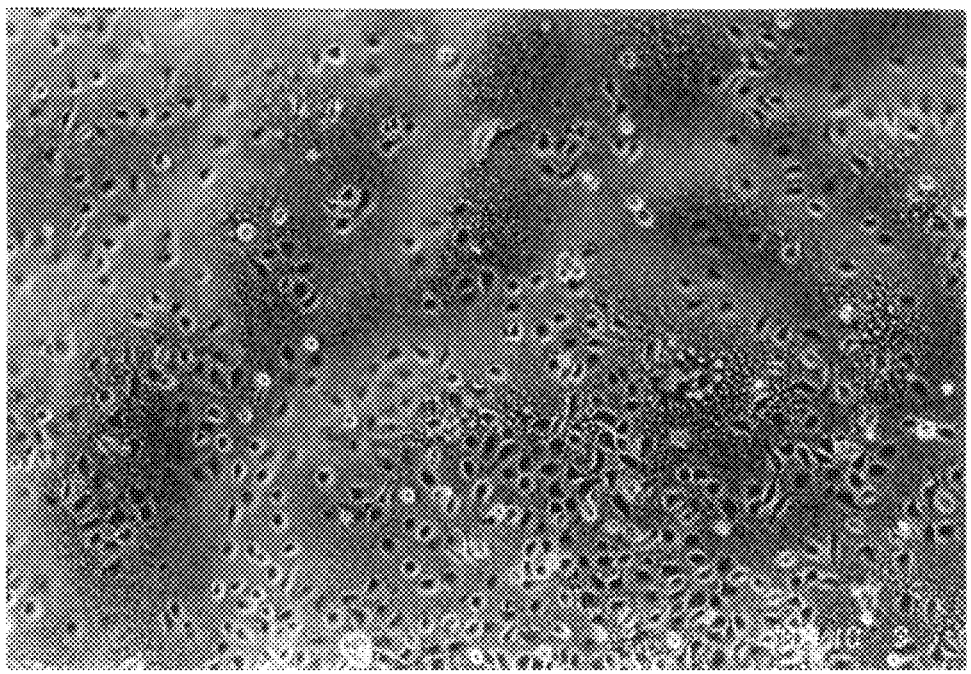
Figure 3A:
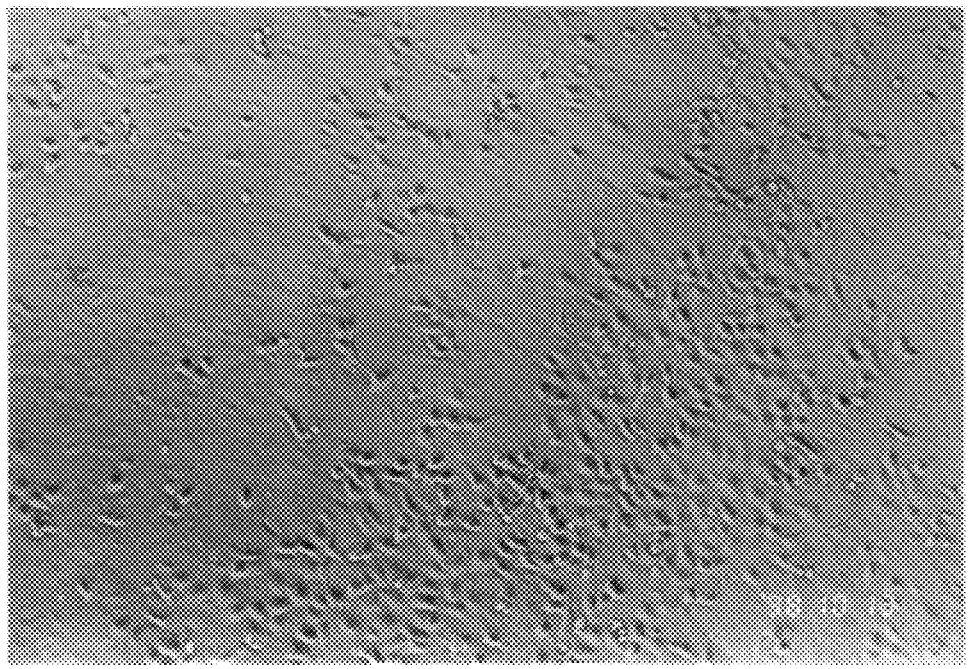
FIGS. 3A and 3B respectively show the adhesion morphology of endothelial cells on an unmodified PU slide and a modified PU slide according to Embodiment 1 of this invention.
Figure 3B:
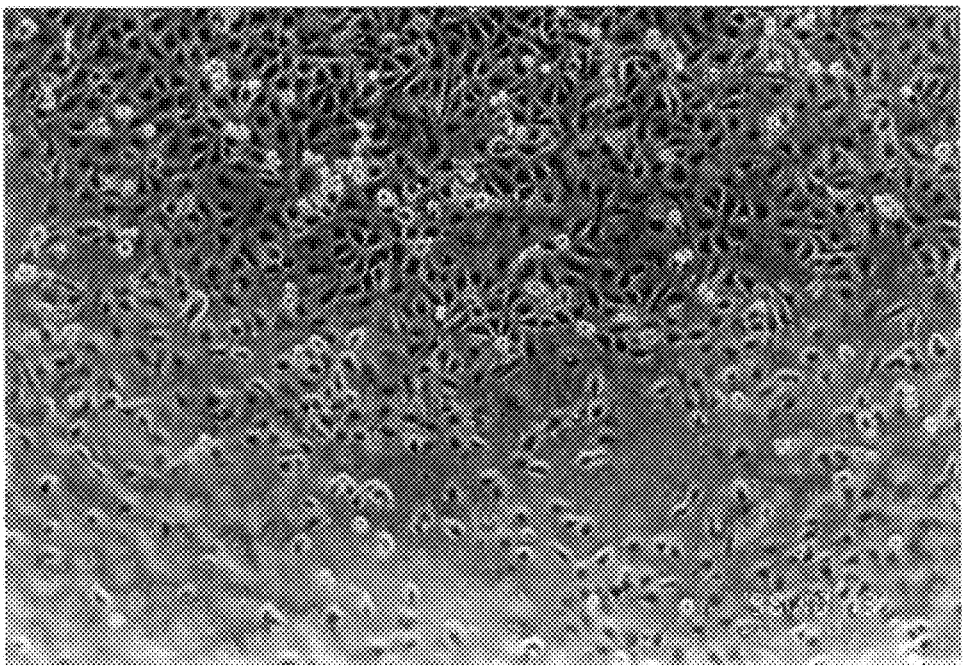

After incubation for 12 hours, the stretch of the cells adhered on both unmodified PU material or PU modified with CBD-RGD containing peptide was observed by a phase-contrast microscope. The results are shown in FIG. 1 to FIG. 3. As shown in the figures, fibroblasts, epithelial cells and endothelial cells adhered more tightly and spread more widely on PU slides modified with CBD-RGD containing peptide (FIGS. 1B, 2B, 3B) than on unmodified PU slides (FIGS. 1A, 2A, 3A). Taking endothelial cells as an example, the area of PU slide modified with CBD-RGD covered by endothelial cells was 2–3 fold of the area of unmodified PU slide covered by endothelial cells. The area of the modified PU covered by fibroblasts is 2 fold of the area of the unmodified PU covered by fibroblasts. The area of the modified PU covered by the epithelial cells is 1–2 fold of the area of the unmodified PU covered by epithelial cells.

According to above data, the adherence and growth of the tissue repairing cells on PU slide modified by coating the CBD-RGD containing peptide thereon were highly enhanced. Specifically, this modification produces results equal to or better than those achieved by the conventional methods using low M.W. RGD containing peptide to modify the surfaces of the PU biomaterial.

Embodiment 2

Artificial Vessels Modified With Cross-linked Gelatin and CBD-RGD Containing Peptide Material The artificial vessels used in this embodiment were made from commercially obtained PU from PELLETHANE 2363-80A (Upjohn Co. Ltd., Torrance Calif.). Also, other commercial PU (e.g. PELLETHANE 2103-80A or CARDIOMAT) can be used. Alternatively, the PU material can be obtained by polymerizing the di-phenyl methane di-isocyanate with polyether glycols.

CBD-RGD protein was prepared according to the previous patent applicant (TW Patent Application No. 86114750 and U.S. patent application Ser. No. 09/166,966). The CBD-RGD stock solution (0.19 mg/ml, 98%) [200 mM Tris-HCl (pH=7.4), 100 mM NaCl, 20 mM $CaCl_2$] remains active after storage in a freezer (−18° C.) for half a year. This CBD-RGD stock solution was warmed to room temperature when used.

Artificial Vessels

The method used to make the artificial vessels in this embodiment were completed by dipping and casting in a solvent mixed with salts (Uchida et al., *J. Biomed. Mater. Res.*, 1993, 27, 1269–79; Wu et al., *Annual Symposium of the Biomedical Engineering Society*, ROC 1997, p.90–91). First, the PU material was dissolved in a 10% DMF solvent, then salt powder of 4-fold by weight of PU was added to form a mixture. The salt powder was sieved with a #400 mesh to provide powder with a diameter less than 37 μm. Next, a glass bar with a diameter of 4 mm and a length of 20 cm was dipped into the mixture for a period of time, then this glass bar was pulled up from the mixture and baked to dry. By repeatedly dipping, pulling-up and baking a number of times (usually 4 times), the outer diameter of the glass bar was coated with a PU layer with an outer diameter of 5 mm, measured by a micrometer. After evaporating the solvent in a vacuum oven, the glass bar was soaked in warm water to dissolve the salt, then a microporous PU vessel with an inner diameter of 4 mm and a thickness of 0.5 mm was obtained after unfastening from the glass bar. The PU vessel obtained according to the process described above was cut into a length of 4 cm.

The Modification Method for Artificial Vessel

Cross-linked gelatin modified artificial vessel: The microporous PU vessel with an inner diameter of 4 mm and a thickness of 0.5 mm was dipped into ethanol to rinse. Then the PU vessel was transferred to a warm gelatin solution (Type B gelatin, commercially obtained from Fisher Scientific Company). Next, the vessel coated with a gelatin layer was transferred to a 4° C. refrigerator to allow the gelatin layer form a gelatin gel. Following, the vessel was dipped into a epoxide solution consisting of DENACOL ($C_8H_{14}O_4$). (EX-810, Nagase Company, Japan) under a dark 4° C. surrounding for 2 days, allowing the DENACOL ($C_8H_{14}O_4$) to crosslink with the gelatin gel coated on the vessel. Accordingly, a cross-linked gelatin modified vessel was obtained.

(2) Cross-linked Gelatin and CBD-RGD Containing Peptide Modified Artificial Vessel The cross-linked gelatin modified vessel obtained according to the previous step was further modified with CBD-RGD containing peptide. First, 0.5 ml of CBD-RGD containing peptide solution was filled into the artificial vessel and incubated stationary in a 37° C. incubator for 30 minutes. Next, the CBD-RGD containing peptide solution within the artificial vessel was removed. Then an artificial vessel with an inner surface modified with a cross-linked gelatin and CBD-RGD containing peptide was obtained.

Adhering Method for Cell

The endothelial cells used in this invention were obtained from ATCC ECV304 cell line. The culture medium used for cultivating ECV304 cells was Medium-199 supplied with 10% FCS. First, 1.5 ml of suspension with a cell density of $1.8 \times 10^6$ cells/ml was prepared, then 0.5 ml of the suspension was introduced into a vessel obtained according to the previous process, and incubated in a 37° C. 5% CO2/95% air incubator for 1 hour. Next, the suspension was removed and replaced with 0.5 ml of fresh suspension, and incubated for 1 hour. Finally, the suspension was removed and replaced with 0.5 ml of the suspension, and incubated for 2.5 hours. The total time needed for cells to adhere cells on the inner surface of the vessel was 5.5 hours.

The Counting of Adhered Cells

As described above, the adhered cells were trypsinized by the trypsin-EDTA solution, then the culture medium was added to neutralize the trypsin. The trypsinized cells were re-suspended and counted by a cell counter.

Flush Experiment

A peristaltic pump was used to provide a culture medium with a flux of 220 ml/min. to continuously flush the cells-adhered artificial vessel at 37° C. for 1 hour. Then the remaining cells on the artificial vessel were counted according to the previous process. The total data were statistically analyzed by Student's t-test.

Test of Platelet Activation

First, the PU-salt powders were melted on a plate to form a porous PU membrane, and subsequently cleaved into circular slides with a diameter of 1.5 cm. Next, the slides were modified with cross-linked gelatin according to the processes described above. Next, 20 µl of CBD-RGD containing peptide solution was dropped on the center of the slide to allow the CBD-RGD containing peptide solution cover the whole slide and adsorb onto the cross-linked gelatin. Finally, the slide was held stationary and incubated in an incubator for 30 minutes to finish the modification.

The test of platelet activation was performed according to following steps. Each modified circular slide was placed into each well of the 24-well microplate (the inner diameter of the well is the same as the diameter of the slide), then 0.5 ml of platelet-rich plasma (containing $4 \times 10^8$ platelets) from a blood bank was introduced into each well of the 24-well microplate, and incubated in a 37° C. 5% $CO_2$/95% air incubator for 1 hour. Then, a portion of the platelets attached on slide were trypsinized by trypsin-EDTA solution, and counted by a cell counter. In order to observe the morphology of the platelets adhered on the slide by a SEM, other cell-adhered slides were fixed by glutaraldehyde, dehydrated by a gradient alcohol, and plated with gold after drying at critical point. The morphologies of platelets were classified into five types (Class 0, 0.25, 0.50, 0.75, 1.0) (Ko et al., *Biomaterials*, 1993, 14, 657–64). Class 0 means the platelet is circular and unactivated; Class 0.25 means platelet has branched pseudopods but is not yet depressed; Class 0.50 means platelet has depressed stretch pseudopods; Class 0.75 means platelet has smear pseudopods but unfolded cytoplasm; and Class 1.0 means platelet is unfolded overall and the pesudopod is disappeared. The average degree of activation of platelets was calculated from the average value of activities of 100 platelets, wherein the activation ranged form 0 to 1. The normalized number of activated platelets was obtained by multiplying the counted platelets with the average degree of activation.

The number of endothelial cells adhered on various slides (unmodified PU, cross-linked gelatin modified PU, CBD-RGD modified PU, and cross-linked gelatin/CBD-RGD modified PU) and the retention rate after flush are listed in Table 3. The definition of retention rate is the ratio of remaining endothelial cell number on slide verse the original adhered endothelial cell number. The unit of cell number in Table 3 was $10^5$ cells. Each sample was triplicated, and the adhered cell number of each sample was counted three times. The flush of adhered cells on various PU slides was repeated at least twice, and counted at least three times.

TABLE 3

|  | Number of adhered cells | Retention rate |
|---|---|---|
| Unmodified PU | 1.7 ± 0.2 | 32 ± 5% |
| PU modified with cross-linked gelatin | 2.1 ± 0.1* | 109 ± 1%*† |
| PU modified with CBD-RGD containing peptide | 2.2 ± 0.1* | 58 ± 1%* |
| PU modified with cross-linked gelatin and CBD-RGD containing peptide | 2.5 ± 0.1* | 113 ± 5%*† |

*means the value was larger than that of unmodified PU and significant when $p < 0.001$.
†means the value was larger than that of PU modified with CBD-RGD and significant when $p < 0.001$.

As shown in Table 3, the number of endothelial cells adhered on PU vessel modified with both cross-linked gelatin and CBD-RGD containing peptide was 30% higher than that of endothelial cells adhered on unmodified PU vessel. The number of endothelial cells adhered on PU vessel modified with both cross-linked gelatin and CBD-RGD containing peptide was 10% higher than that of endothelial cells adhered on PU vessel modified with only either cross-linked gelatin or CBD-RGD containing peptide. After continuously flushing for 1 hour, the retention rate of endothelial cells adhered on the PU vessel modified with cross-linked gelatin and CBD-RGD containing peptide was 3 fold of that adhered on unmodified PU vessel, 2 fold of that adhered on PU modified with only CBD-RGD containing peptide, and 10% higher than that adhered on PU modified with only cross-linked gelatin.

Since the endothelial cells continuously differentiated during flushing, thus the number of endothelial cells adhered on the slide was increased instead of decreasing. In particular, the shear stress was helpful to promote endothelial cells to differentiate (Ott et al., Endothelium, 1995, 3, 21–30).

As published in literatures (Kempczinski, R. F., Douville, E. C., Ramalanjaona, G., Ogie, J. D. and Sibewrstein, E. B. Endothelial cell seeding on a fibronectin-coated substrate. In: *Endothelial Seeding in Vascular Surgery*, M. Herring and J. L. Glover, ed., Grune & Stratton, Orlando, Fla., 1987), after in-vivo flushing for 1 hour, the retention rate of endothelial cells adhered on a PTFE vessel was about 60%, and the retention rate of endothelial cells adhered on a natural fibronectin-modified vessel was about 80%. Moreover, after flushing for 10 hours, the retention rate of endothelial cells on either unmodified PTFE vessel or fibronectin-modified vessel was 36% and 65%, respectively. Comparing this date with that of the CBD-RGD modified PU vessel indicates that modification leads to little flush-resistance (with a retention rate of 58%). However, as shown in Table 3, the retention rate was enhanced to 113% when the PU was modified with both cross-linked gelatin and CBD-RGD containing peptide. Accordingly, the flush-resistance of PU vessel can be highly enhanced by modifying with both gelatin and CBD-RGD containing peptide.

The results of adherence and activation of platelets on various PU vessels are listed in Table 4.

TABLE 4

|  | Number of adhered platelets | Average degree of activation | Normalized number of activated platelets |
|---|---|---|---|
| Unmodified PU | 10.0 ± 0.3 | 1.00 | 10.0 ± 0.2 |
| PU modified with cross-linked gelatin | 6.2 ± 0.2* | 0.41* | 2.6 ± 0.2* |
| PU modified with CBD-RGD containing peptide | 8.5 ± 0.2* | 0.64* | 5.4 ± 0.5* |
| PU modified with cross-linked gelatin and CBD-RGD containing peptide | 6.9 ± 0.2* | 0.09*† | 0.6 ± 0.1*† |

*means the value was less than that of unmodified PU and significant when $p < 0.001$.
†means the value was the lowest among all samples and significant when $p < 0.001$.

As shown in Table 4, the number of adhered platelets was significantly reduced when the modified PU vessel was used (e.g. PU vessel modified with cross-linked gelatin, PU vessel modified with CBD-RGD containing peptide, and PU vessel modified with both cross-linked gelatin and CBD-RGD containing peptide). Similarly, the average degree of activation of platelets and the normalized number of actived platelets on modified PU were significantly reduced when comparing with the platelets on unmodified PU. In particular, the average degree of activation of platelets and the number of activated platelets on the PU modified with cross-linked gelatin and CBD-RGD containing peptide were both the lowest among all samples in Table 4. Accordingly, the results in Table 4 indicate that the CBD-RGD containing peptide coated on PU can inhibit the adhesion and agglutination of platelets.

According to the results in Tables 3 and 4, by modifying the inner surface of the microporous PU vessels with cross-linked gelatin and CBD-RGD containing peptide, the adhering number and flush-resistance of endothelial cells can be highly enhanced. Moreover, the number of active platelets on modified PU can be significantly reduced. Consequently, an ideal artificial vessel can be obtained by modification with cross-linked gelatin and CBD-RGD containing peptide.

From the above description, one skilled in this art can easily ascertain the essential characteristics of the present invention, and, without departing from the spirit and scope thereof, can make various changes and modifications of the invention to adapt it to various usage and conditions. Thus, other embodiments also fall within the scope of the following claims.

What is claimed is:

1. A biomedical material for improving the adhesion and proliferation of tissue cells, comprising:

a biomedical substrate consisting of PU for cells to attach thereon; and a surface modifier consisting of CBD-RGD containing peptide directly and non-covalently coated on the surface of the biomedical substrate, wherein the molecular weight of the CBD-RGD containing peptide is approximately 13 kDa.

2. The biomedical material as claimed in claim 1, wherein the biomedical material is a tissue culture plate.

3. A biomedical material for improving the adhesion and proliferation of tissue cells, comprising:

a biomedical substrate consisting of PU for cells to attach thereon; and a surface modifier consisting of CBD-RGD containing peptide coated on the surface of the biomedical substrate, wherein the molecular weight of the CBD-RGD containing peptide is approximately 13 kDa.

4. A method for making a biomedical material for improving the adhesion and proliferation of tissue cells, comprising:

providing a biomedical substrate consisting of PU for attachment of cells; and directly and non-covalently coating a CBD-RGD containing peptide layer on the biomedical substrate, wherein the molecular weight of the CBD-RGD containing peptide is approximately 13 kDa.

5. The method as claimed in claim 4, wherein the biomedical substrate is a cell culture plate.

6. A method for making a biomedical material for improving the adhesion and proliferation of tissue cells, comprising:

providing a biomedical substrate consisting of PU for attachment of cells; and coating a CBD-RGD containing peptide layer on the biomedical substrate, wherein the molecular weight of the CBD-RGD containing peptide is approximately 13 kDa.

* * * * *